(12) United States Patent
Chung et al.

(10) Patent No.: US 10,526,373 B2
(45) Date of Patent: Jan. 7, 2020

(54) PEPTIDE SHOWING MELANIN GENERATION-PROMOTING ACTIVITY AND USE THEREOF

(71) Applicant: CAREGEN CO., LTD., Anyang-si (KR)

(72) Inventors: Yong Ji Chung, Yongin-si (KR); Eun Mi Kim, Yongin-si (KR); Eung-Ji Lee, Anyang-si (KR); Jan Di Kim, Seoul (KR)

(73) Assignee: Caregen Co., Ltd., Anyang-si (KR)

( * ) Notice: Subject to any disclaimer, the term of this patent is extended or adjusted under 35 U.S.C. 154(b) by 0 days.

(21) Appl. No.: 15/999,692

(22) PCT Filed: Feb. 13, 2017

(86) PCT No.: PCT/KR2017/001526
§ 371 (c)(1),
(2) Date: Aug. 20, 2018

(87) PCT Pub. No.: WO2017/142264
PCT Pub. Date: Aug. 24, 2017

(65) Prior Publication Data
US 2019/0119321 A1   Apr. 25, 2019

(30) Foreign Application Priority Data
Feb. 18, 2016   (KR) .................. 10-2016-0019310

(51) Int. Cl.
| | | |
|---|---|---|
| *C07K 7/06* | (2006.01) | |
| *C07K 7/08* | (2006.01) | |
| *A61K 38/08* | (2019.01) | |
| *A61K 8/64* | (2006.01) | |
| *A61Q 19/00* | (2006.01) | |
| *C07K 14/495* | (2006.01) | |
| *C12N 9/02* | (2006.01) | |

(52) U.S. Cl.
CPC .................. *C07K 7/06* (2013.01); *A61K 8/64* (2013.01); *A61K 38/08* (2013.01); *A61Q 19/00* (2013.01); *C07K 7/08* (2013.01); *C07K 14/495* (2013.01); *C12N 9/0071* (2013.01); *C12Y 114/18001* (2013.01)

(58) Field of Classification Search
None
See application file for complete search history.

(56) References Cited

U.S. PATENT DOCUMENTS

| 6,696,417 B1 | 2/2004 | Raghupathi et al. |
| 7,057,013 B1 | 6/2006 | Ezquerro Saenz et al. |
| 2010/0104521 A1 | 4/2010 | Dal Farra et al. |
| 2017/0051014 A1 | 2/2017 | Chung et al. |

FOREIGN PATENT DOCUMENTS

| EP | 2394666 A2 | 12/2011 |
| JP | 2002-501012 A | 1/2002 |
| KR | 10-0889460 B1 | 3/2009 |
| KR | 10-2011-0130282 A | 12/2011 |
| KR | 10-2015-0130615 A | 11/2015 |
| WO | WO-2015/081306 A2 | 6/2015 |
| WO | WO-2015/174599 A1 | 11/2015 |

OTHER PUBLICATIONS

Fields, "Conditions of the Eye and Ear: Albinism", Nevada Dual Sensory Impairment Project, 2014, p. 9 (Year: 2014).*
Shaffer, "Special disorders of Black Skin", The Washington Post, 1985, pp. 1-3 (Year: 1985).*
Busca et al., "Cyclic AMP a key messenger in the regulation of skin pigmentation," Pigment Cell Res. 13(2):60-9 (2000).
Sarkar et al., "Human placental protein/peptides stimulate melanin synthesis by enhancing tyrosinase gene expression," Mol Cell Biochem. 285(1-2):133-42 (2006).
Supplementary Partial European Search Report dated Oct. 15, 2018 for European Patent Application No. 17753425.2, Chung et al., "Peptide Showing Melanin Generation-Promoting Activity, and Use Thereof," filed Feb. 13, 2017 (10 pages).
International Search Report dated Jun. 7, 2017 for International Patent Application No. PCT/KR2017/001526, Chung et al., "Peptide Showing Melanin Generation-Promoting Activity, and Use Thereof," filed Feb. 13, 2017 (6 pages).
Kim et al., "Transforming growth factor-beta1 decreases melanin synthesis via delayed extracellular signal-regulated kinase activation," Int J Biochem Cell Biol. 36(8):1482-91 (2004).
Extended European Search Report dated Mar. 14, 2019 for European Patent Application No. 18214157.2, Chung et al., "Peptide Showing Melanin Generation-Promoting Activity, and Use Thereof," filed Feb. 13, 2017 (7 pages).
Murakami et al., "Regulation of melanin synthesis by the TGF-beta family in B16 melanoma cells," Mol Biol Rep. 36(6):1247-50 (2009); published online Jul. 4, 2008.

* cited by examiner

*Primary Examiner* — Lianko G Garyu
(74) *Attorney, Agent, or Firm* — Clark & Elbing LLP; Susan M. Michaud (57) ABSTRACT

The present invention provides a peptide which shows a melanin generation-promoting activity. The peptide of the present invention increases the activity and expression of tyrosinase and increases the expression of factors related to melanin generation, thereby showing an excellent effect in melanin generation. The peptide of the present invention can be used for preventing, alleviating, and treating hypomelanosis. The above-mentioned superior activity and stability of the peptide of the present invention allows the peptide to be very favorably applied to medicines, quasi drugs, and cosmetics.

18 Claims, 9 Drawing Sheets
Specification includes a Sequence Listing.

SEQUENCE LISTING

<160> NUMBER OF SEQ ID NOS: 8

<210> SEQ ID NO 1
<211> LENGTH: 8
<212> TYPE: PRT
<213> ORGANISM: Artificial Sequence
<220> FEATURE:
<223> OTHER INFORMATION: Synthetic Construct

<400> SEQUENCE: 1

Arg Trp Arg Arg Lys Ile Glu Asn
1               5

<210> SEQ ID NO 2
<211> LENGTH: 12
<212> TYPE: PRT
<213> ORGANISM: Artificial Sequence
<220> FEATURE:
<223> OTHER INFORMATION: Synthetic Construct

<400> SEQUENCE: 2

Phe Cys Leu Gly Pro Cys Pro Tyr Ile Trp Ser Leu
1               5                   10

<210> SEQ ID NO 3
<211> LENGTH: 21
<212> TYPE: DNA
<213> ORGANISM: Artificial Sequence
<220> FEATURE:
<223> OTHER INFORMATION: Synthetic Construct

<400> SEQUENCE: 3
ccagcctggc gatcatgtca t                                                 21

<210> SEQ ID NO 4
<211> LENGTH: 20
<212> TYPE: DNA
<213> ORGANISM: Artificial Sequence
<220> FEATURE:
<223> OTHER INFORMATION: Synthetic Construct

<400> SEQUENCE: 4
ggtctggaca ggagttgctg                                                   20

<210> SEQ ID NO 5
<211> LENGTH: 20
<212> TYPE: DNA
<213> ORGANISM: Artificial Sequence
<220> FEATURE:
<223> OTHER INFORMATION: Synthetic Construct

<400> SEQUENCE: 5
ggccagcttt caggcagagg                                                   20

<210> SEQ ID NO 6
<211> LENGTH: 20
<212> TYPE: DNA
<213> ORGANISM: Artificial Sequence

```
<220> FEATURE:
<223> OTHER INFORMATION: Synthetic Construct

<400> SEQUENCE: 6
tggtgcttca tgggcaaaat                                               20

<210> SEQ ID NO 7
<211> LENGTH: 20
<212> TYPE: DNA
<213> ORGANISM: Artificial Sequence
<220> FEATURE:
<223> OTHER INFORMATION: Synthetic Construct

<400> SEQUENCE: 7
tctgtgaagg tgtgcaggag                                               20

<210> SEQ ID NO 8
<211> LENGTH: 20
<212> TYPE: DNA
<213> ORGANISM: Artificial Sequence
<220> FEATURE:
<223> OTHER INFORMATION: Synthetic Construct

<400> SEQUENCE: 8
ccgaaacaga gtggaaggtt                                               20
```

PEPTIDE SHOWING MELANIN GENERATION-PROMOTING ACTIVITY AND USE THEREOF

SEQUENCE LISTING

The instant application contains a Sequence Listing which has been submitted electronically in ASCII format and is hereby incorporated by reference in its entirety. Said ASCII copy, created on Aug. 14, 2018 is named 50413-208001_ARTSYNTH_Sequence_Listing_8.14.18_ST25 and is 1,866 bytes in size.

TECHNICAL FIELD

The present invention relates to a peptide having an activity to stimulate melanogenesis, a pharmaceutical composition containing the peptide as an active ingredient for preventing and/or treating hypomelanosis, a cosmetic composition containing the peptide as an active ingredient for preventing and/or alleviating hypomelanosis, and a use of the peptide for preventing, improving and/or treating hypomelanosis.

BACKGROUND ART

Skin cells produce melanin in melanosomes of melanocytes that are present in the basal epidermal layer, as a defense mechanism for the stimulation of ultraviolet light, environmental pollution, and other external factors. Melanin is an important factor to determine the color of skin, eyes, and hair of animals. Hypomelanosis is also known as a risk factor of skin cancer. Asians are sensitive to the overproduction of melanin, and thus many whitening-related studies for melanogenesis inhibition have been conducted. In recent years, the demand against vitiligo, which is caused by melanogenesis inhibition, is also increasing, and thus studies therefor are being conducted.

Vitiligo is an acquired decolorizing disease wherein milky spots of several sizes and shapes are shown due to apoptosis or necrosis of melanocytes. Vitiligo is a relatively common disease that occurs in about 1% of the population around the world, and there is no difference in the disease by race or area. Regarding the occurrence ages, vitiligo occurs most frequently at ages of 10 to 30 years, with 95% occurring before the age of 40, and 30% of the patients have a family history.

The causes of vitiligo have not yet been accurately revealed, but there are various theories, such as autoimmune hypothesis, neural hypothesis, and melanocyte self-destruct hypothesis. The autoimmune hypothesis is that the destruction or dysfunction of melanocytes is caused by the expression of auto-antibodies to melanocytes-based antigens, or melanocytes are destroyed by lymphokines secreted by cytotoxic lymphocytes or activated lymphocytes. The neural hypothesis is that hydrogen peroxide associated with stress is generated due to abnormal catecholamine biosynthesis and increased monoamine oxidase, resulting in the destruction of melanocytes, and vitiligo may occur along the ganglion or vitiligo may occur after nerve damage or stress. The melanocytes self-destruct hypothesis is that intermediate metabolites or phenol complexes as final metabolite of the melanogenic process are accumulated in melanocytes, resulting in cell destruction. Besides, various factors, such as inherent cellular defects, genetic factors, apoptosis, calcium metabolic disorders, are suggested.

Melanin is synthesized from melanocytes, and plays an important role in skin protection by the irradiation of UV light or the absorption of toxic substances and chemical substances. Therefore, people having no occurrence of normal melanin synthesis have an appearance problem in that the skin becomes white in part rather than whole, causing spots, and have a severe problem of being sensitive to external stimulations.

Tyrosinase, tyrosinase related protein-1 (TRP-1), and tyrosinase related protein-2 (TRP-2), which are important enzymes in melanin synthesis, act as catalysts for oxidative reactions (Pigment Cell Res. 14 (6): 43744).

Here, tyrosinase acts to oxidize tyrosine into L-3,4-dihydroxyphenylalanine (DOPA) and DOPA into DOPA quinine, and TRP-1 is dihydroxyindole carboxylic acid oxidase and involved in the conversion of 5,6-dihydroxyindole-2-carboxylic acid (DHICA) into indol-5,6-quinone-2-carboxylic acid. TRP-1 also serves to stabilize tyrosinase and regulate activity thereof. TRP-2, which is the DOPA chrome tautomerase, converts DOPA chrome into DHICA to form eumelanon and pheomelanon, constituting melanocytes, and the ratio thereof determines the colors of skin, hair, eyes, and the like.

The melanin synthesis is activated by UV irradiation and α-melanocyte stimulating hormone (MSH). Here, α-MSH, which is a peptide hormone, is known to be produced by ultraviolet light and made from several cells including those of the pituitary gland and skin.

Here, α-MSH acts on melanocortin receptors (MCR) of melanocytes by paracrine to regulate the activity of the transcription factor microphthalmia-associated transcription factor (MITF), thereby regulating the activity of tyrosinase, DHICA oxidase (TRP-1), DOPAchrometautomerase (TRP-2), and the like, which play important roles in melanin synthesis (THE JOURNAL OF BIOLOGICAL CHEMISTRY Vol. 273, No. 31, Issue of July 31, pp. 195609565, 1998).

It has been reported that the stimulation of melanocytes by UV or α-MSH leads to the activation of tyrosinase by p38 or protein kinase A (PKA), respectively. In these two pathways, especially, the α-MSH→cAMP→PKA pathway plays an important role in melanin synthesis. The increase in cAMP stimulates the phosphorylation of cAMP-responsive element binding protein (CREB), increasing the expression of the transcription factor MITF, which enhances the activity of tyrosinase and increases the mRNA expression of tyrosinase (Nucleic Acids Res. 30 (14): 3096106, Pigment Cell Melanoma Res 21 (6): 66576).

Asian people including Koreans want to have light skin colors, and thus have conducted many studies about whitening components inhibiting melanogenesis. However, melanin is synthesized from melanocytes in the skin, and plays an important role in skin protection by the irradiation of UV or the absorption of toxic substances and chemical substances. Since the absence of normal synthesis of melanin makes the skin sensitive to external stimulation and shows abnormal external appearances, the treatment for normal melanin synthesis is needed and studies therefor have been also conducted. So far, the development of techniques for stimulating melanin synthesis has not been sufficiently conducted.

DETAILED DESCRIPTION OF THE INVENTION

Technical Problem

The present inventors endeavored to develop peptides capable of stimulating melanogenesis, and as a result, the present inventors confirmed that a peptide consisting of the amino acid sequence of SEQ ID NO: 1 or SEQ ID NO: 2 has excellent melanogenesis stimulatory activity and established that these peptides can be favorably used in the prevention and treatment of hypomelanosis, and thus the present inventors completed the present invention.

Therefore, an aspect of the present invention is to provide a peptide showing melanogenesis stimulatory activity, the peptide being composed of an amino acid sequence of SEQ ID NO: 1 or SEQ ID NO: 2.

Another aspect of the present invention is to provide a pharmaceutical composition for preventing or treating hypomelanosis, the pharmaceutical composition containing, as an active ingredient, at least one peptide selected from the group consisting of a peptide consisting of the amino acid sequence of SEQ ID NO: 1 and a peptide consisting of the amino acid sequence of SEQ ID NO: 2.

Another aspect of the present invention is to provide a cosmetic composition for preventing or alleviating hypomelanosis, the cosmetic composition containing, as an active ingredient, at least one peptide selected from the group consisting of a peptide consisting of the amino acid sequence of SEQ ID NO: 1 and a peptide consisting of the amino acid sequence of SEQ ID NO: 2.

Technical Solution

In accordance with an aspect of the present invention, there is provided a peptide having an activity to stimulate melanogenesis, the peptide consisting of the amino acid sequence of SEQ ID NO: 1 or SEQ ID NO: 2.

The present inventors endeavored to develop peptides capable of stimulating melanogenesis, and as a result, the present inventors confirmed that a peptide consisting of the amino acid sequence of SEQ ID NO: 1 or SEQ ID NO: 2 has excellent melanogenesis stimulatory activity and established that these peptides can be favorably used in the prevention and treatment of hypomelanosis.

The peptide of the present invention may include the amino acid sequence of SEQ ID NO: 1 or SEQ ID NO: 2, and for example, may be composed of the amino acid sequence of SEQ ID NO: 1 or SEQ ID NO: 2.

The peptide of the present invention is obtained by screening peptides, which have excellent melanogenesis stimulatory effects, from peptide libraries possessed by the present inventors, through experiments about gene and protein expression changes or the like, and a total of two types of peptides are provided as a peptide of the present invention.

As used herein, the term "peptide" refers to a linear molecule formed of amino acid residues link to each other via peptide linkages. The peptide of the present invention may be prepared by known chemical synthesis methods, especially, solid-phase synthesis techniques (Merrifield, J. Amer. Chem. Soc. 85:2149-54(1963); Stewart, et al., Solid Phase Peptide Synthesis, 2nd. ed., Pierce Chem. Co.: Rockford, 111(1984)) or liquid-phase synthesis techniques (U.S. Pat. No. 5,516,891).

The peptide of the present invention may have a modification induced at the N-terminal or C-terminal thereof in order to select a part of an amino acid sequence and increase the activity thereof.

For example, the C-terminal modification may be a modification of the C-terminal of the peptide into a hydroxy group (—OH), an amino group (—NH$_2$), an azide group (—NHNH$_2$), or the like, but is not limited thereto.

In addition, the N-terminal modification may be an attachment of at least one protecting group selected from the group consisting of an acetyl group, a fluorenyl methoxy carbonyl group, a formyl group, a palmitoyl group, a myristyl group, a stearyl group, and polyethylene glycol (PEG) to the N-terminal of the peptide, but is not limited thereto. The protecting group protects the peptide of the present invention from in vivo protein cleavage enzymes.

The N-terminal and/or C-terminal modification of the peptide improves the stability of the peptide, and this modification allows the peptide of the present invention to have an increased half-life at the time of in vivo administration, thereby having a high half-life.

As used herein, the term "stability" refers to storage stability (e.g., room-temperature stability) as well as in vivo stability.

According to an aspect of the present invention, the peptide of the present invention increases the production of melanin in melanocytes, increases the activity and expression of tyrosinase, which is an enzyme for regulating melanin synthesis, increases the expression of MITF and TRP1 and increases the phosphorylation of CREB, these being factors involved in melanogenesis.

These results indicate that the peptide of the present invention has an effect of relieving leukoplakia by increasing melanogenesis. Therefore, the peptide of the present invention can be used for the prevention, improvement, and/or treatment of hypomelanosis.

In the present invention, the hypomelanosis may be vitiligo, albinism, nevus depigmentosus, pityriasis alba, pityriasis versicolor, post-inflammatory depigmentation, morphea, piebaldism, idiopathic guttate hypomelanosis, and/or leucoderma punctatum, but is not limited thereto.

In accordance with another aspect of the present invention, there is provided a pharmaceutical composition for preventing or treating hypomelanosis, the pharmaceutical composition containing, as an active ingredient, at least one peptide selected from the group consisting of a peptide consisting of the amino acid sequence of SEQ ID NO: 1 and a peptide consisting of the amino acid sequence of SEQ ID NO: 2.

Since the composition of the present invention contains the foregoing peptide of the present invention as an active ingredient, the descriptions of overlapping contents therebetween will be omitted to avoid excessive complexity of the present specification.

The composition of the present invention, when prepared as a pharmaceutical composition, may contain a pharmaceutically effective amount of the foregoing peptide of the present invention.

In addition, the pharmaceutical composition may further contain a pharmaceutically acceptable carrier, but is not limited thereto.

As used herein, the term "pharmaceutically effective amount" refers to an amount sufficient to attain the efficacy or activity of the foregoing peptide.

The pharmaceutically acceptable carrier contained in the pharmaceutical composition of the present invention is ordinarily used at the time of formulation, and examples thereof may include, but are not limited to, lactose, dextrose, sucrose, sorbitol, mannitol, starch, acacia gum, calcium phosphate, alginate, gelatin, calcium silicate, microcrystalline cellulose, polyvinylpyrrolidone, cellulose, water, syrup, methyl cellulose, methyl hydroxybenzoate, propyl hydroxybenzoate, talc, magnesium stearate, and/or mineral oil.

The pharmaceutical composition of the present invention may further contain a lubricant, a wetting agent, a sweetening agent, a flavoring agent, an emulsifier, a suspending agent, a preservative, and the like, in addition to the above ingredients.

The pharmaceutical composition of the present invention is preferably administered parenterally, and for example, may be administered by topical skin administration.

The appropriate dose of the pharmaceutical composition of the present invention varies depending on factors, such as a formulating method, a manner of administration, patient's age, body weight, gender, morbidity, food, a time of administration, a route of administration, an excretion rate, and response sensitivity. The ordinarily skilled practitioners can easily determine and prescribe the dose that is effective for the desired treatment or prevention. According to a preferable embodiment of the present invention, the daily dose of the pharmaceutical composition of the present invention is 0.001-1000 mg/kg.

The pharmaceutical composition of the present invention is formulated using a pharmaceutically acceptable carrier and/or excipient according to a method that is easily conducted by a person having ordinary skills in the art to which the present invention pertains, and the pharmaceutical composition of the present invention may be prepared into a unit dosage form or may be inserted into a multi-dose container. Here, the dosage form may be a solution in an oily or aqueous medium, a suspension, an emulsion, an extract, a powder, granules, a tablet, a capsule, or a gel (e.g., a hydrogel), and may further contain a dispersing agent or a stabilizer.

In accordance with still another aspect of the present invention, there is provided a cosmetic composition for preventing or alleviating hypomelanosis, the cosmetic composition containing, as an active ingredient, at least one peptide selected from the group consisting of a peptide consisting of the amino acid sequence of SEQ ID NO: 1 and a peptide consisting of the amino acid sequence of SEQ ID NO: 2.

When the composition of the present invention is prepared as a cosmetic composition, the composition may contain a cosmetically effective amount of the foregoing peptide of the present invention.

In addition, the cosmetic composition may further contain a cosmetically acceptable carrier, but is not limited thereto.

As used herein, the term "cosmetically effective amount" refers to an amount sufficient to attain the efficacy of the foregoing composition of the present invention.

The cosmetic composition of the present invention may be formulated into any dosage form that is conventionally prepared, and examples thereof may include a solution, a suspension, an emulsion, a paste, a gel, a cream, a lotion, a powder, a soap, a surfactant-containing cleanser, an oil, a powder foundation, an emulsion foundation, a wax foundation, and a spray, but are not limited thereto. More specifically, the cosmetic composition of the present invention may be prepared in a dosage form of emollient lotion, nourishing lotion, nourishing cream, massage cream, essence, eye cream, cleansing cream, cleansing foam, cleansing water, pack, spray, and/or powder.

In cases where the dosage form of the cosmetic composition is a paste, cream, or gel, useful examples of the carrier ingredient may include an animal oil, a plant oil, wax, paraffin, starch, tragacanth, a cellulose derivative, polyethylene glycol, silicone, bentonite, silica, talc, and/or zinc oxide, but is not limited thereto.

In cases where the dosage form of the cosmetic composition is a powder or spray, lactose, talc, silica, aluminum hydroxide, calcium silicate, or a polyamide powder may be used as a carrier ingredient, but is not limited thereto. Especially, in cases where the dosage form of the present invention is a spray, the spray may further include a propellant, such as chlorofluorohydrocarbon, propane/butane, or dimethyl ether, but is not limited thereto.

In cases where the dosage form of the cosmetic composition is a solution or emulsion, a solvent, solubilizer, or emulsifier may be used as a carrier component, and examples thereof include water, ethanol, isopropanol, ethyl carbonate, ethyl acetate, benzyl alcohol, benzyl benzoate, propylene glycol, 1,3-butyl glycol oil, glycerol aliphatic esters, polyethylene glycol, and/or fatty acid esters of sorbitan.

In cases where the dosage form of the cosmetic composition is a suspension, useful examples of the carrier ingredient may include a liquid diluent (such as water, ethanol, and/or propylene glycol), a suspending agent (such as ethoxylated isostearyl alcohol, polyoxyethylene sorbitol ester, and/or polyoxyethylene sorbitan ester), microcrystalline cellulose, aluminum metahydroxide, bentonite, agar, and/or tragacanth, but are not limited thereto.

In cases where the dosage form of the cosmetic composition is a surfactant-containing cleanser, useful examples of the carrier ingredient may be aliphatic alcohol sulfate, aliphatic alcohol ether sulfate, sulfosuccinate monoester, isethionate, imidazolium derivatives, methyl taurate, sarcosinate, fatty acid amide ether sulfate, alkyl amido betaine, aliphatic alcohol, fatty acid glyceride, fatty acid diethanolamide, plant oil, lanoline derivatives, and/or ethoxylated glycerol fatty acid ester, but are not limited thereto.

The ingredients contained in the cosmetic composition of the present invention may include, in addition to the peptide and carrier ingredients as active ingredients, ingredients ordinarily used in cosmetic compositions, for example, ordinary supplements, such as an antioxidant, a purifier, a solubilizer, vitamins, a pigment and/or a flavoring agent, but are not limited thereto.

Advantageous Effects

The present invention is directed to a peptide having an activity to stimulate melanogenesis, a pharmaceutical composition containing the peptide as an active ingredient for preventing and/or treating hypomelanosis, a cosmetic composition the peptide as an active ingredient for preventing and/or improving hypomelanosis, and a use of the peptide for preventing, improving and/or treating hypomelanosis. The peptide of the present invention increases the activity and expression of tyrosinase and increases the expression of factors involved in melanogenesis, thereby exhibiting excellent effects in melanogenesis, and can be very advantageously applied to medicines, quasi-medicines, and cosmetics through excellent activity and safety thereof.

BEST MODE FOR CARRYING OUT THE INVENTION

Provided is a peptide having an activity to stimulate melanogenesis, the peptide consisting of the amino acid sequence of SEQ ID NO: 1 or 2.

MODE FOR CARRYING OUT THE INVENTION

Hereinafter, the present invention will be described in detail with reference to examples. These examples are only for illustrating the present invention more specifically, and it will be apparent to those skilled in the art that the scope of the present invention is not limited by these examples.

EXAMPLES

Synthetic Example 1: Peptide Synthesis 700 mg of chlorotrityl chloride resin (CTL resin, Nova Biochem Cat No. 01-64-0021) was added into a reaction container, and 10 ml of methylene chloride (MC) was added, followed by stirring for 3 minutes. After the solution was removed, 10 ml of dimethyl form amide (DMF) was added, followed by stirring for 3 minutes, and then the solvent was again removed.

10 ml of a dichloromethane solution was added to a reactor, and 200 mmole Fmoc-Asp(OtBu)-OH (Bachem, Swiss) and 400 mmole diisopropyl ethylamine (DIEA) were added. Thereafter, the mixture was well dissolved with stirring, and then the reaction was conducted with stirring for 1 hour.

After the reaction, washing was conducted, and then methanol and DIEA (2:1) were dissolved in dichloromethane (DCM), followed by reaction for 10 minutes, and then the resulting material was washed with excess DCM/DMF (1:1). After the solution was removed, 10 ml of dimethyl form amide (DMF) was added, followed by stirring for 3 minutes, and then the solvent was again removed.

10 ml of a deprotection solution (20% piperidine/DMF) was added to a reaction container, followed by stirring at room temperature for 10 minutes, and then the solution was removed. An equal amount of a deprotection solution was added, and then the reaction was again maintained for 10 minutes, and thereafter, the solution was removed, followed by washing twice with DMF, once with MC, and once with DMF, for 3 minutes each, thereby preparing Ser (tBu)-CTL resin.

10 ml of a DMF solution was added to a new reactor, and 200 mmol Fmoc-Thr(tBu)-OH (Bachem, Swiss), 200 mmol HoBt, and 200 mmole Bop were added, and the mixture was well dissolved with stirring. 400 mmole DIEA was added to a reactor in two divided portions, and then stirring was conducted for at least 5 minutes until all solids were dissolved.

The dissolved amino acid mixed solution was added to the reaction container containing the deprotected resin, and the reaction was conducted with stirring at room temperature for 1 hour. After the reaction solution was removed, the stirring was conducted using a DMF solution three times for 5 minutes each, followed by removal.

A small amount of the reaction resin was taken to check the extent of reaction using the Kaiser test (Ninhydrin test). The deprotection reaction was twice conducted using a deprotection solution in the same manner as described above, thereby preparing Glu(OtBu)-Asp(OtBu)-CTL resin.

After sufficient washing with DMF and MC, the Kaiser test was again conducted, and then the following amino acid attachment test was conducted in the same manner as described above.

A chain reaction was conducted in the order of Fmoc-Ile-OH, Fmoc-Lys(Boc)-OH, Fmoc-Arg(Pbf)-OH, Fmoc-Arg(Pbf)-OH, Fmoc-Trp-OH, and Fmoc-Arg(Pbf)-OH on the basis of the selected amino acid sequence. The Fmoc-protecting group was removed by reaction twice with the deprotection solution for 10 minutes for each and then favorable washing.

Acetic anhydride, DIEA, and HoBt were added to conduct acetylation for 1 hour, and then the prepared peptidyl resin was washed with DMF, MC, and methanol three times for each, dried under the flow of nitrogen gas, and completely dried by decompression under vacuum in $P_2O_5$.

Thereafter, 30 ml of a leaving solution [95% trifluoroacetic acid (TFA), 5% distilled water 2, and 5% thioanisole 2] was added, and the reaction was maintained for 2 hours while the mixture was intermittently stirred at room temperature.

The resin was obtained through filtration, washed with a small amount of a TFA solution, and then mixed with the stock solution. The distillation was conducted under reduced pressure to reduce the total volume by half, and then 50 ml of cold ether was added to induce precipitation.

Thereafter, the precipitates were collected by centrifugation, followed by washing twice with cold ether. The stock solution was removed, followed by sufficient drying under nitrogen atmosphere, thereby synthesizing 0.65 g of unpurified peptide 1, Arg-Trp-Arg-Arg-Lys-Ile-Glu-Asn (yield: 92.0%).

The molecular weight was determined as 1157.3 (theoretical value: 1157.33) by using a molecular weight analysis system. In addition, the peptide composed of the amino acid sequence of SEQ ID NO: 2 was synthesized by the method as described above.

TABLE 1

| SEQ ID NO | Sequence (5'->3') | Analysis value (Mass spectrometer) | |
|---|---|---|---|
| | | Analytical value | Theoretical value |
| 1 | Arg-Trp-Arg-Arg-Lys-Ile-Glu-Asn | 1157.3 | 1157.33 |
| 2 | Phe-Cys-Leu-Gly-Pro-Cys-Pro-Tyr-Ile-Trp-Ser-Leu | 1398.7 | 1398.7 |

Example 1: Melanogenesis Assay

After melanocytes (B16F10 cell line) in 6-well plates were cultured in an incubator at 37° C. for 24 hours, the medium of each plate was removed and exchanged with fresh medium, followed by treatment with the present peptide at different concentrations. After the incubation for 72 hours, the culture medium was removed, and the cells were taken off and then transferred into 5-ml tubes, followed by centrifugation at 13,000 rpm for 3 minutes. The supernatant was removed, and cell pellets were collected to observe melanin. Then, 150 µl of 2 M NaOH was added to the cell pellets to lyse intracellular melanin at 60° C. for 30 minutes. Then, 100 µl of the supernatant obtained from the lysis was added into each well of 96-well plates, and the absorbance was measured at 490 nm. The results are shown in FIGS. 1a and 1b.

Figure 1A:
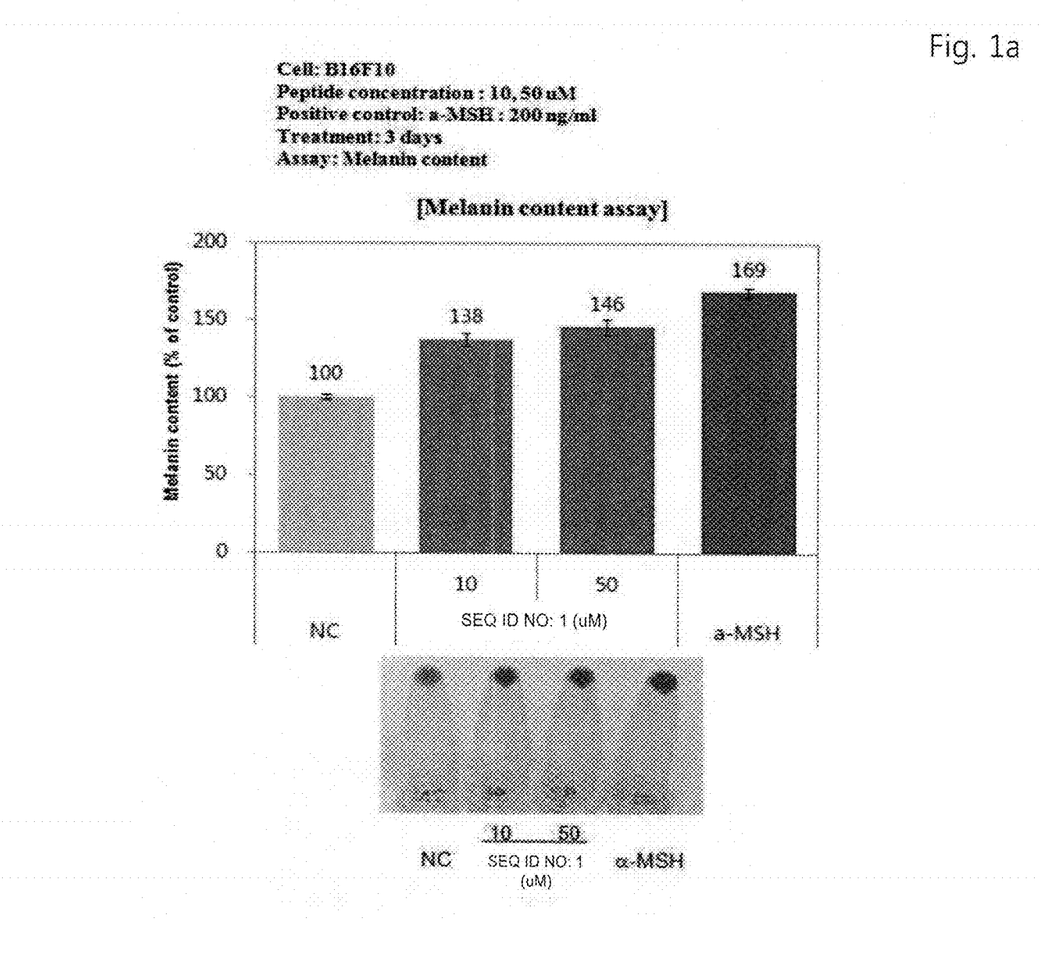
FIG. 1a shows the results of confirming a melanogenesis increasing effect by a peptide composed of the amino acid sequence of SEQ ID NO: 1 according to an embodiment of the present invention.
Figure 1B:
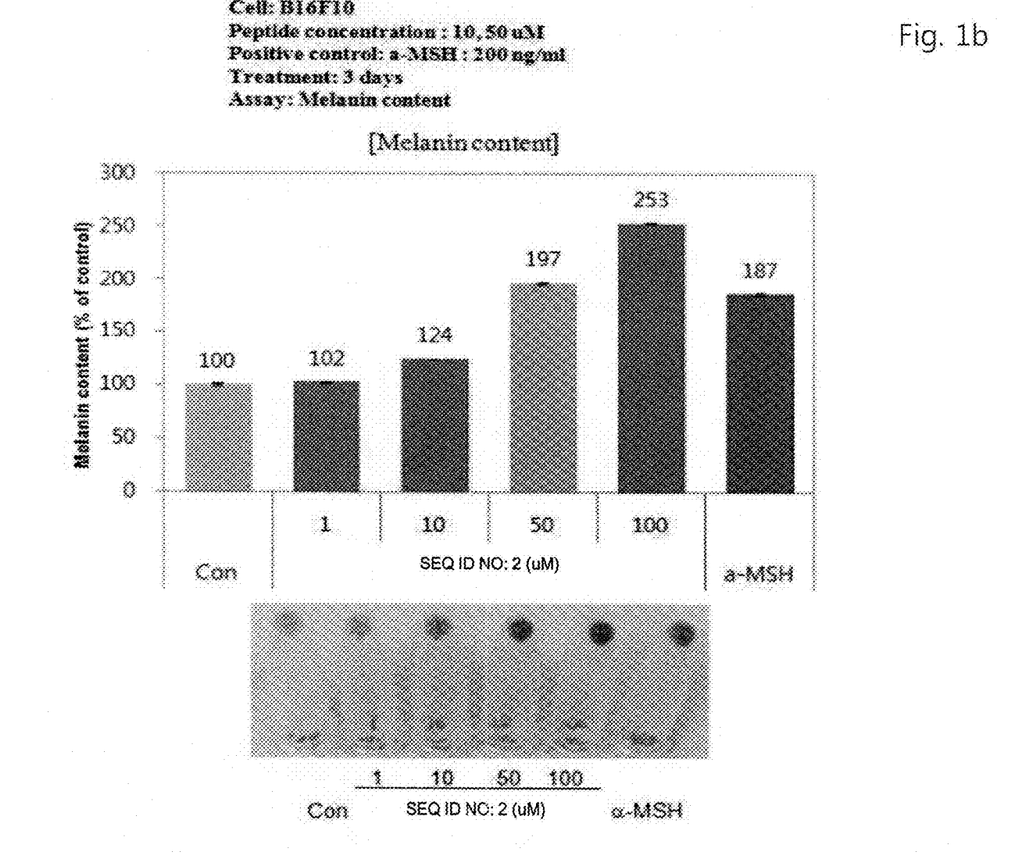
FIG. 1b shows the results of confirming a melanogenesis increasing effect by a peptide composed of the amino acid sequence of SEQ ID NO: 2 according to an embodiment of the present invention.

As can be confirmed in FIGS. 1a and 1b, melanogenesis was increased when the mouse melanin cell line B16F10 was treated with the peptide composed of the amino acid sequence of SEQ ID NO: 1 or 2.

Example 2: Tyrosinase Activity Assay

Melanoma cell line (B16F10) cells were cultured in 6-well culture plates for 24 hours, and treated with the peptide with difference concentrations, followed by culture for 72 hours. The 6-well culture plates were loaded on ice and washed with cool PBS, and then 300 µl of 0.1 M sodium phosphate buffer (pH 6 lysis buffer) containing 1% Triton X-100 was added. The cells were collected in 1.5-mL tubes, and then cell membranes were disrupted by repeating five times rapid-freezing at −270° C. and thawing. After centrifugation at 13,000 rpm for 20 minutes, the supernatant was collected in other 1.5-mL tubes, and the protein of the samples was quantified. The samples were diluted to have the same protein concentration and then dispensed in every three wells in 96-well culture plates, and then 20 µl of 10 mM L-dopa was added, followed by incubation at 37° C. for 1 hour. The absorbance was measured at 475 nm.

Figure 2A:
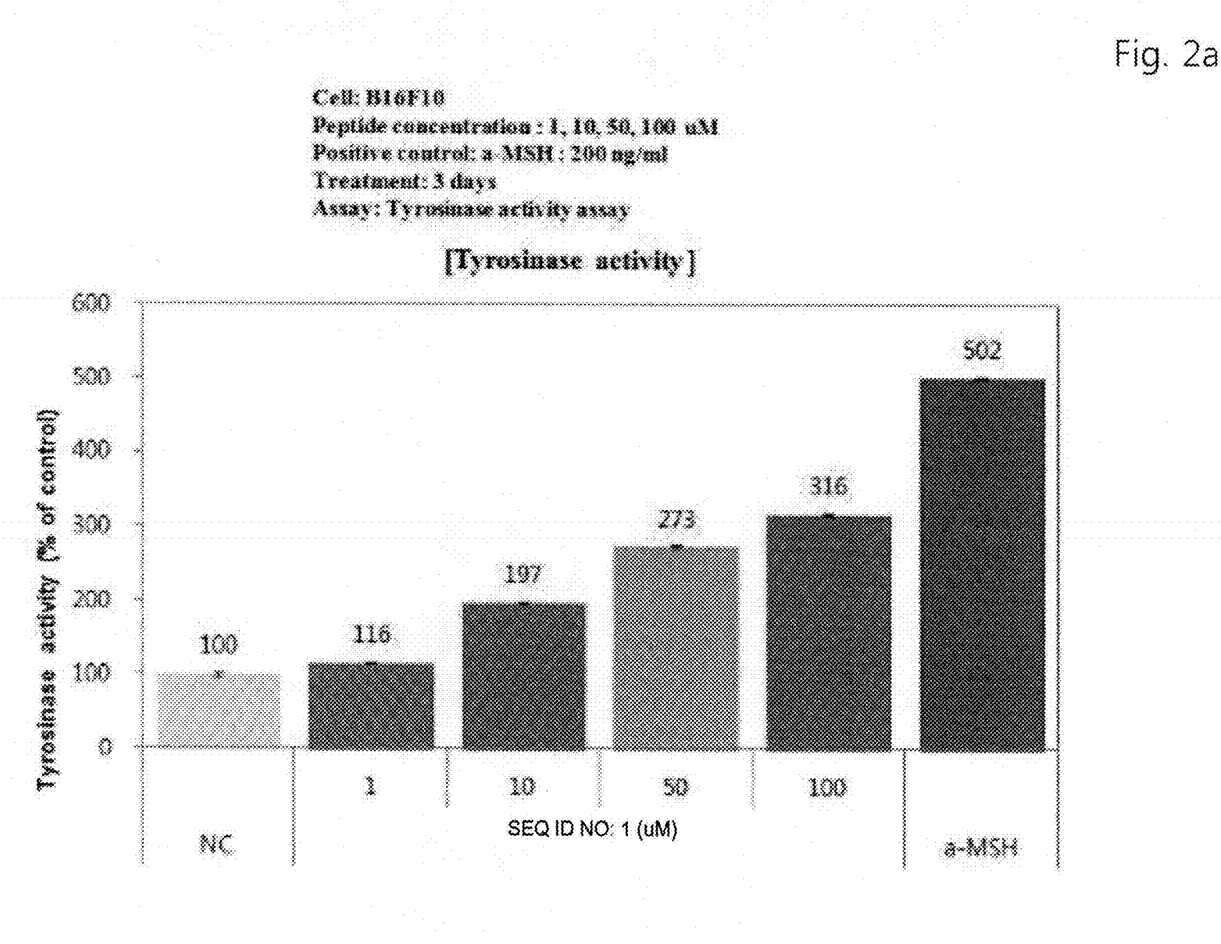
FIG. 2a shows the results of confirming a tyrosinase activity increasing effect by a peptide composed of the amino acid sequence of SEQ ID NO: 1 according to an embodiment of the present invention.
Figure 2B:
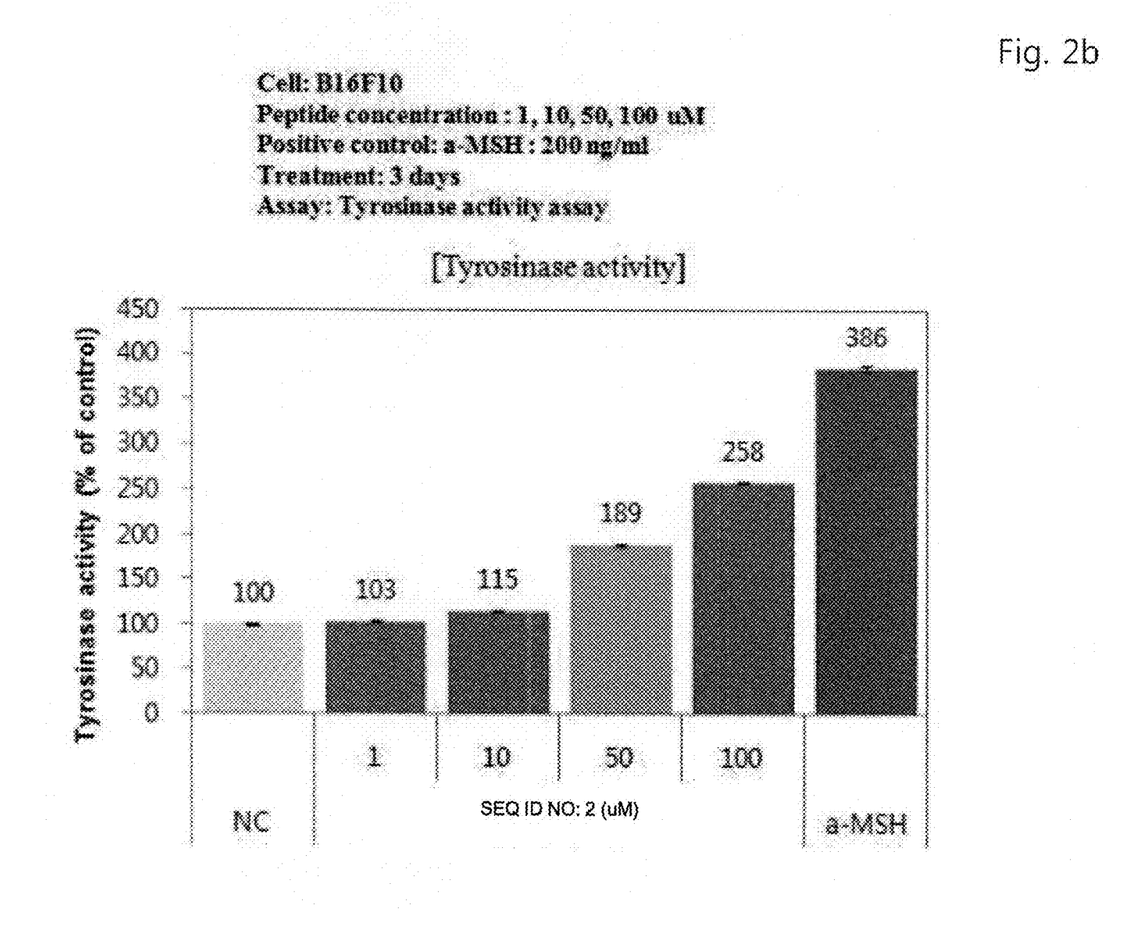
FIG. 2b shows the results of confirming a tyrosinase activity increasing effect by a peptide composed of the amino acid sequence of SEQ ID NO: 2 according to an embodiment of the present invention.

As can be confirmed from FIGS. 2a and 2b, tyrosinase activity was increased when mouse melanin cell line B16F10 was treated with the peptide composed of the amino acid sequence of SEQ ID NO: 1 or 2

Example 3: RT-PCR of Melanogenesis-Related Genes

Melanocytes (B16F10 cell line) were incubated on 6-well culture plates in an incubator for 24 hours, and were treated with the peptides of the present invention with different concentrations. After RNA was extracted from the cells incubated for 72 hours, cDNA was prepared. PCR was performed by using respective primers specific to MITF and tyrosinase, which are the factors involved in melanogenesis, and the expression changes of the respective genes were observed. The results are shown in FIGS. 3a and 3b.

TABLE 2

| SEQ ID NO | Primer name | Sequence (5'-3') |
|---|---|---|
| 3 | MITF_F | CCAGCCTGGCGATCATGTCAT |
| 4 | MITF_R | GGTCTGGACAGGAGTTGCTG |
| 5 | tyrosinase_F | GGCCAGCTTTCAGGCAGAGG |
| 6 | tyrosinase_R | TGGTGCTTCATGGGCAAAAT |
| 7 | TRP1_F | TCTGTGAAGGTGTGCAGGAG |
| 8 | TRP1_R | CCGAAACAGAGTGGAAGGTT |

Figure 3A:
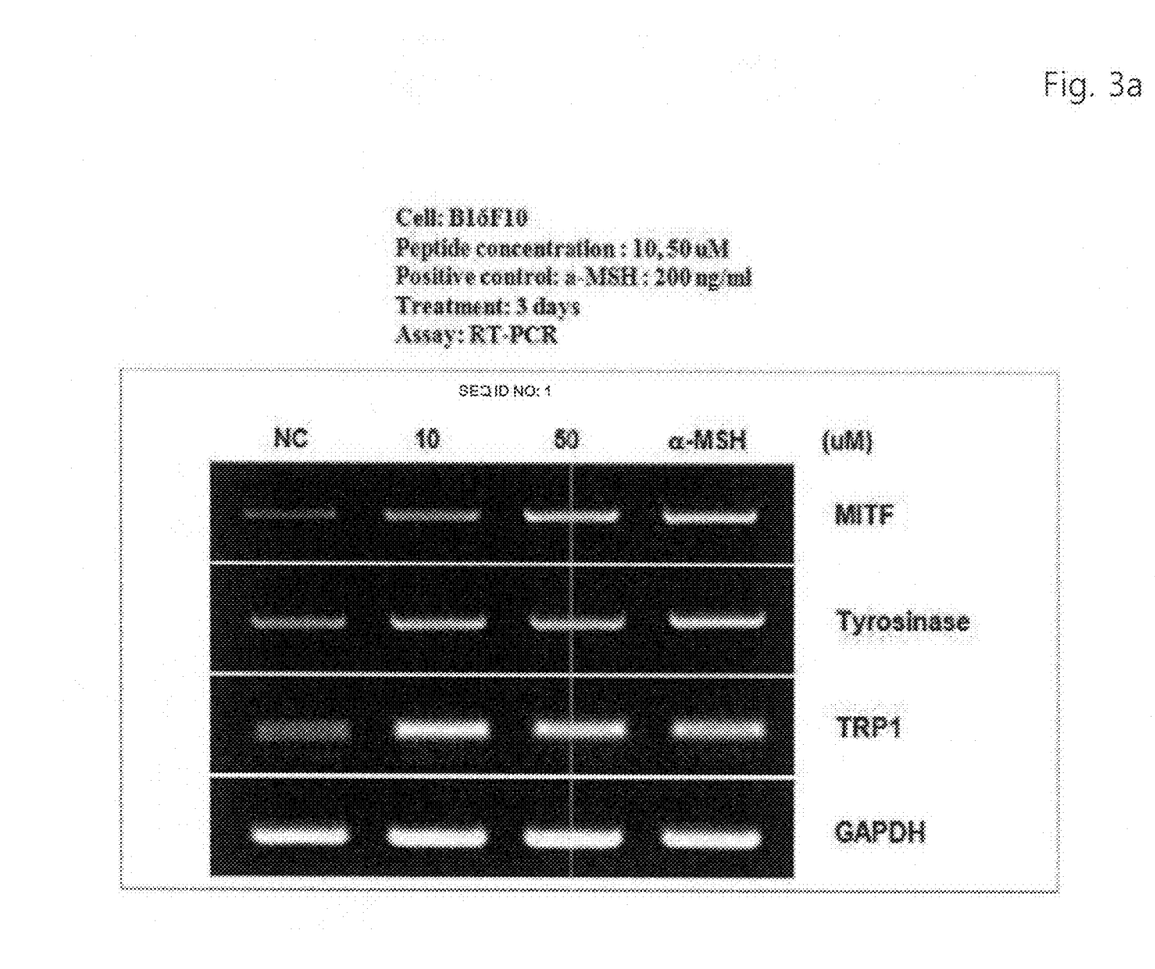
FIG. 3a shows the results of confirming mRNA expression increases of MITF, tyrosinase, and TRP1 by a peptide composed of the amino acid sequence of SEQ ID NO: 1 according to an embodiment of the present invention.
Figure 3B:
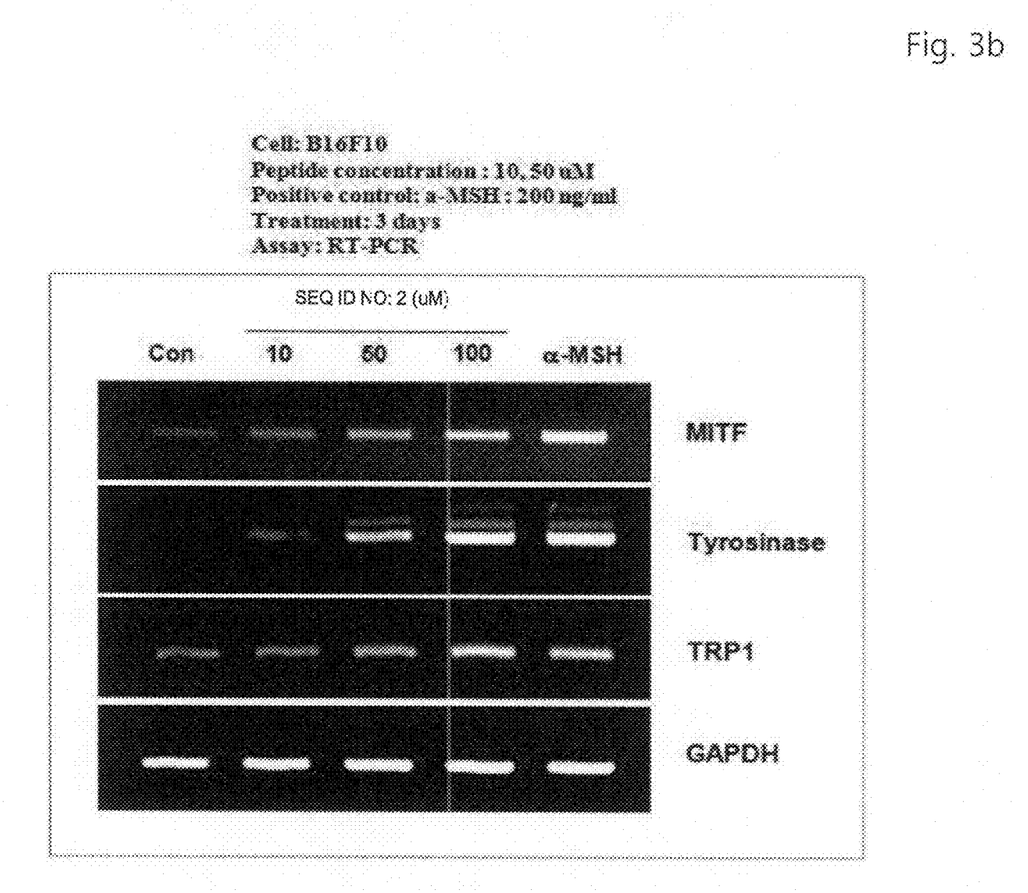
FIG. 3b shows the results of confirming mRNA expression increases of MITF, tyrosinase, and TRP1 by a peptide composed of the amino acid sequence of SEQ ID NO: 2 according to an embodiment of the present invention.

As can be confirmed in FIGS. 3a and 3b, the mRNA expression of MITF, tyrosinase, and TRP1, which are transcriptional factors involved in melanogenesis, were increased when the mouse melanin cell line B16F10 was treated with the peptide composed of the amino acid sequences of SEQ ID NO: 1 or SEQ ID NO: 2.

Example 4: Western Blotting of Melanogenesis-Related Proteins

Melanocytes (B16F10 cell line) were incubated on 6-well culture plates in an incubator for 24 hours, and were treated with the peptides of the present invention with different concentrations. After 72-hour incubation, the cells were lysed, and the cells were subjected to western blotting using specific antibodies (two types, both by Santa Cruz Biotechnology, USA) to investigate the expression of MITF and tyrosinase, which are the factors involved in melanogenesis. The results are shown in FIGS. 4a and 4b.

Figure 4A:
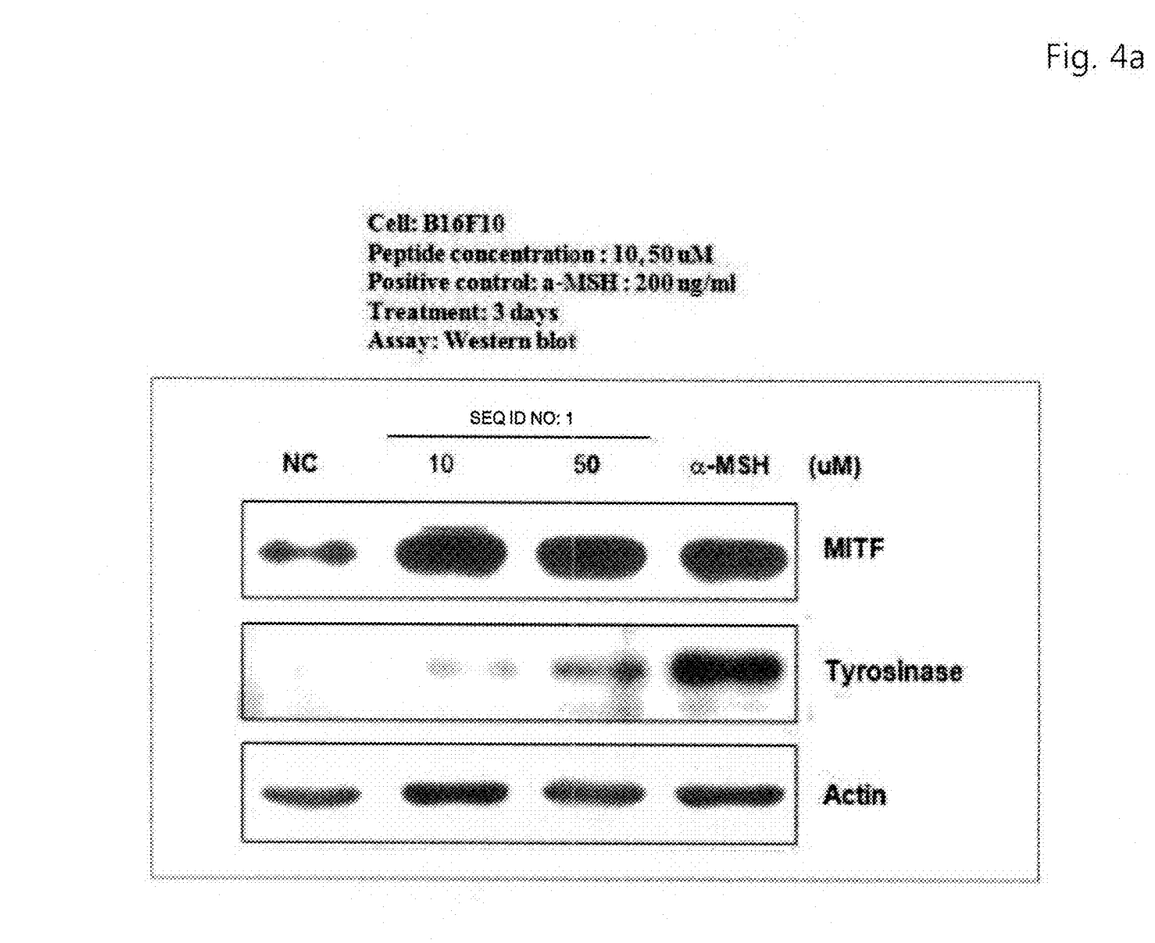
FIG. 4a shows the results of confirming protein expression increases of MITF and tyrosinase by a peptide composed of the amino acid sequence of SEQ ID NO: 1 according to an embodiment of the present invention.

As can be confirmed from FIG. 4a, the protein expression of the MITF transcriptional factor and tyrosinase enzyme, which are involved in melanogenesis, was increased when the mouse melanin cell line B16F10 was treated with the peptide composed of the amino acid sequences of SEQ ID NO: 1.

Figure 4B:
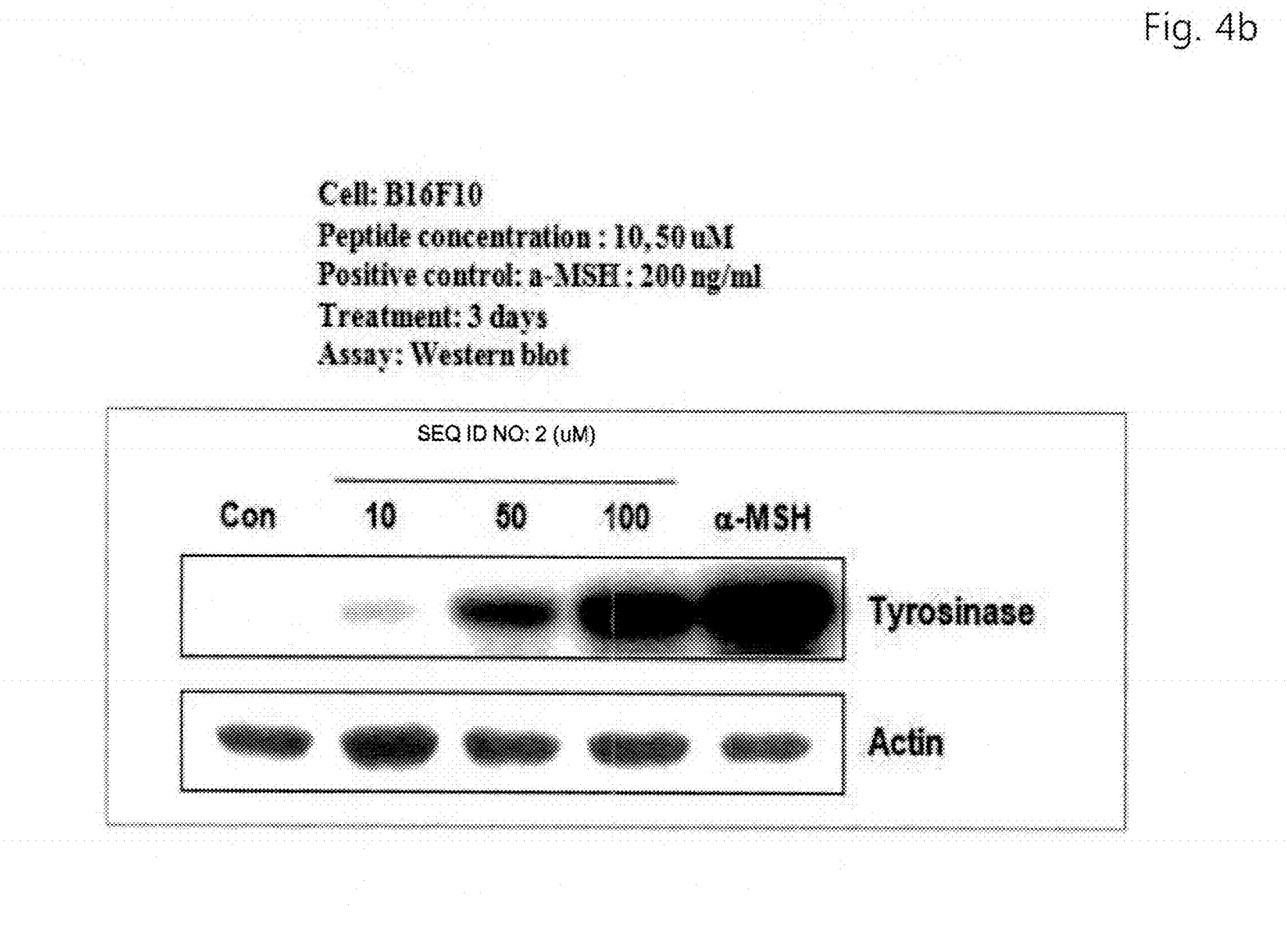
FIG. 4b shows the results of confirming a protein expression increase of tyrosinase by a peptide composed of the amino acid sequence of SEQ ID NO: 2 according to an embodiment of the present invention.

As can also be confirmed from FIG. 4b, the protein expression of tyrosinase, which is involved in melanogenesis, was increased when the mouse melanin cell line B16F10 was treated with the peptide composed of the amino acid sequences of SEQ ID NO: 2.

Example 5: Melanogenesis-Related Protein Activity Assay

Melanocytes (B16F10 cell line) were incubated on 6-well culture plates in an incubator for 24 hours, and were treated with the peptide of the present invention with different concentrations. After 72-hour incubation, the cells were lysed, and the cells were subjected to western blotting using specific antibodies (Cell Signaling Technology, USA) to investigate the phosphorylation level of CREB, which is a signaling substance involved in melanogenesis. The results are shown in FIG. 5.

Figure 5:
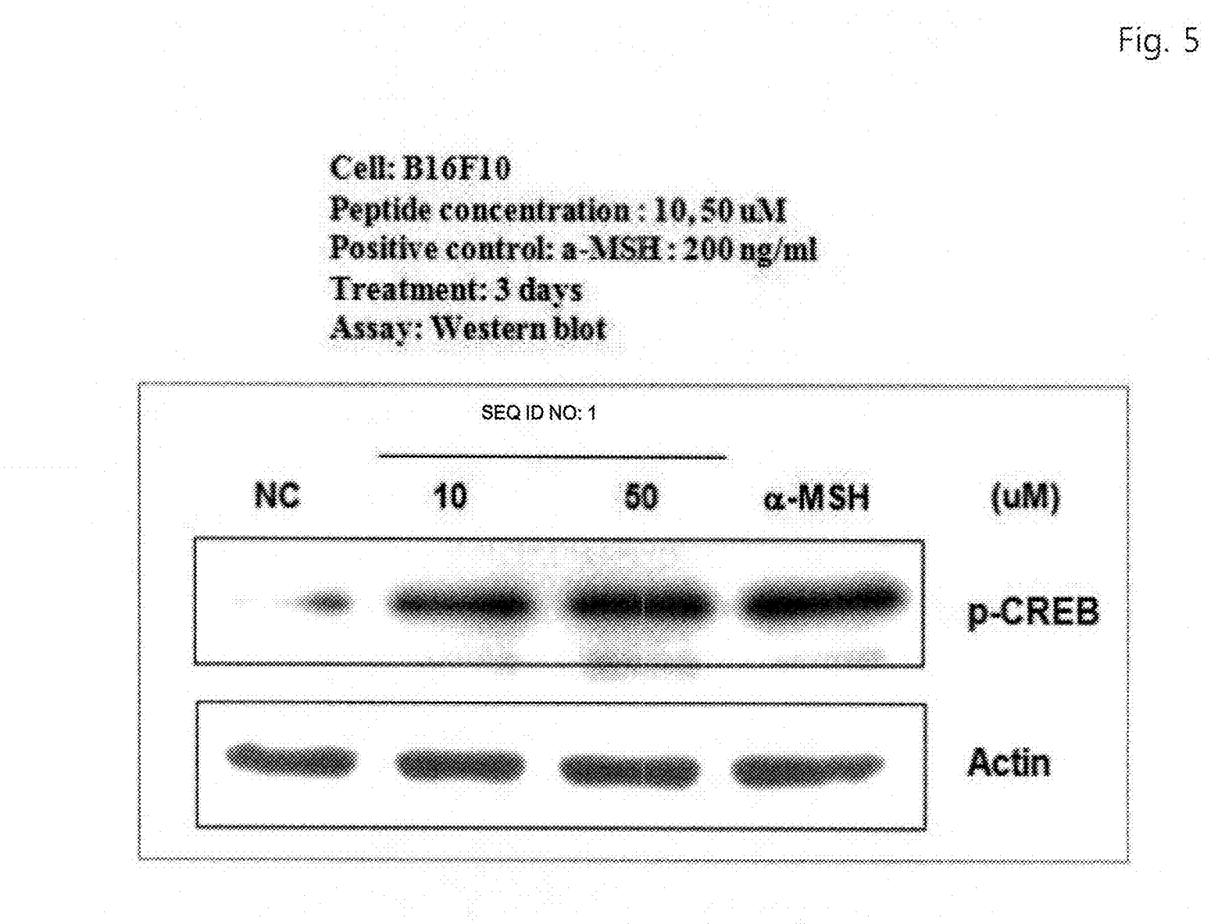
FIG. 5 shows the results of confirming a phosphorylation increase of CREB by a peptide composed of the amino acid sequence of SEQ ID NO: 1 according to an embodiment of the present invention.

As can be confirmed from FIG. 5, the phosphorylation level of CREB, which is a factor involved in melanogenesis, was increased when the mouse melanin cell line B16F10 was treated with the peptide composed of the amino acid sequences of SEQ ID NO: 1.

INDUSTRIAL APPLICABILITY

The present invention relates to a peptide showing melanogenesis stimulatory activity, a pharmaceutical composition containing the peptide as an active ingredient for preventing and/or treating hypomelanosis, a cosmetic composition containing the peptide as an active ingredient for preventing and/or alleviating hypomelanosis, and a use of the peptide for preventing, alleviating and/or treating hypomelanosis.

The invention claimed is:

1. A peptide having an activity to stimulate melanogenesis, the peptide consisting of the amino acid sequence of SEQ ID NO: 1 or SEQ ID NO: 2, optionally wherein (i) the C-terminal end of the peptide is modified by the presence of an amino group or an azide group, or (ii) the N-terminal end of the peptide comprises a protecting group.

2. The peptide of claim 1, wherein the peptide increases the activity of tyrosinase.

3. The peptide of claim 1, wherein the peptide increases the expression of a melanin synthesis-related factor selected from the group consisting of microphthalmia-associated transcription factor (MITF) and tyrosinase-related protein 1 (TRP1).

4. The peptide of claim 1, wherein the peptide increases the expression of tyrosinase.

5. The peptide of claim 1, wherein the peptide increases the phosphorylation of cAMP response element-binding protein (CREB).

6. The peptide of claim 1, wherein the C-terminal end of the peptide is modified by the presence of an amino group or an azide group.

7. The peptide of claim 1, wherein the N-terminal end of the peptide comprises a protecting group.

8. The peptide of claim 7, wherein the protecting group is selected from the group consisting of an acetyl group, a fluorenyl methoxy carbonyl group, a formyl group, a palmitoyl group, a myristyl group, a stearyl group, and polyethylene glycol (PEG).

9. A method for treating hypomelanosis comprising:
administering a pharmaceutical composition comprising at least one peptide selected from a peptide consisting of the amino acid of SEQ ID NO: 1 and a peptide consisting of the amino acid of SEQ ID NO: 2, as an active ingredient, optionally wherein (i) the C-terminal end of the at least one peptide is modified by the presence of an amino group or an azide group, or (ii) the N-terminal end of the at least one peptide comprises a protecting group.

10. The method of claim 9, wherein the hypomelanosis is vitiligo, albinism, nevus depigmentosus, pityriasis alba, pityriasis versicolor, post-inflammatory depigmentation, morphea, piebaldism, idiopathic guttate hypomelanosis, or leucoderma punctatum.

11. The method of claim 9, wherein the C-terminal end of the at least one peptide is modified by the presence of an amino group or an azide group.

12. The method of claim 9, wherein the N-terminal end of the at least one peptide comprises a protecting group.

13. The method of claim 12, wherein the protecting group is selected from the group consisting of an acetyl group, a fluorenyl methoxy carbonyl group, a formyl group, a palmitoyl group, a myristyl group, a stearyl group, and polyethylene glycol (PEG).

14. A method for improving hypomelanosis comprising:
contacting a subject with a cosmetic composition comprising at least one peptide selected from a peptide consisting of the amino acid of SEQ ID NO: 1 and a peptide consisting of the amino acid of SEQ ID NO: 2, as an active ingredient, optionally wherein (i) the C-terminal end of the at least one peptide is modified by the presence of an amino group or an azide group, or (ii) the N-terminal end of the at least one peptide comprises a protecting group.

15. The method of claim 14, wherein the hypomelanosis is vitiligo, albinism, nevus depigmentosus, pityriasis alba, pityriasis versicolor, post-inflammatory depigmentation, morphea, piebaldism, idiopathic guttate hypomelanosis, or leucoderma punctatum.

16. The method of claim 14, wherein the C-terminal end of the at least one peptide is modified by the presence of an amino group or an azide group.

17. The method of claim 14, wherein the N-terminal end of the at least one peptide comprises a protecting group.

18. The method of claim 17, wherein the protecting group is selected from the group consisting of an acetyl group, a fluorenyl methoxy carbonyl group, a formyl group, a palmitoyl group, a myristyl group, a stearyl group, and polyethylene glycol (PEG).

\* \* \* \* \*